United States Patent [19]

Zerbes et al.

[11] Patent Number: 4,632,999
[45] Date of Patent: Dec. 30, 1986

[54] PROCESS FOR THE PREPARATION OF OXIRANES

[75] Inventors: Rudolf Zerbes, Wuppertal, Fed. Rep. of Germany; Siegfried W. Linke, Seoul, Rep. of Korea; Karl H. Mohrmann; Wolf Reiser, both of Wuppertal, Fed. Rep. of Germany

[73] Assignee: Bayer Aktiengesellschaft, Leverkusen, Fed. Rep. of Germany

[21] Appl. No.: 789,987

[22] Filed: Oct. 22, 1985

Related U.S. Application Data

[63] Continuation of Ser. No. 603,524, Apr. 24, 1984, abandoned.

[30] Foreign Application Priority Data

Apr. 29, 1983 [DE] Fed. Rep. of Germany ....... 3315524

[51] Int. Cl.$^4$ .......................................... C07D 301/02
[52] U.S. Cl. .................................................. 549/519
[58] Field of Search ......................................... 549/519

[56] References Cited

U.S. PATENT DOCUMENTS 4,162,258 7/1979 Higo et al. ........................ 549/332
4,230,719 10/1980 Kodama et al. ................... 549/79
4,296,236 10/1981 Christensen et al. .

FOREIGN PATENT DOCUMENTS 40345 11/1981 European Pat. Off. .

OTHER PUBLICATIONS

V. Franzen et al, Berichte, vol. 96 (1963) pp. 1881–1890.
Corey et al, J.A.C.S., vol. 87(6) (1965) pp. 1353–1364.
Corey et al, J.A.C.S., vol. 84(19) (1962) pp. 3782–3783.
Sulfur Ylides in Organic Chemistry, Monograph, Academic Press (1975), pp. 10, 11, 30–35.

T. Kutsuma et al, Heterocyclies, vol. 8 (1977), pp. 397–401.

Primary Examiner—Norma S. Milestone
Attorney, Agent, or Firm—Sprung, Horn, Kramer & Woods

[57] ABSTRACT

A process for the preparation of an oxirane of the formula

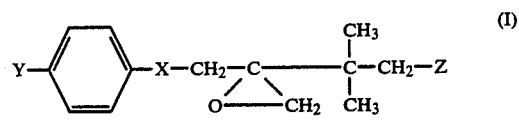

(I)

in which Y represents chlorine or phenyl, X represents oxygen or $CH_2$ and Z represents hydrogen or halogen, which comprises containing dimethyl sulphoxide with dimethyl sulphate whereby to form trimethyloxosulphonium methyl sulphate of the formula

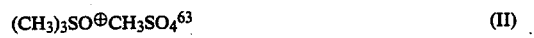

(II)

and thereafter, without isolating said trimethyloxosulphonium methyl sulphate, contacting the same with a ketone of the formula

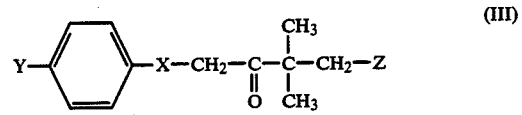

(III)

in which X, Y and Z have the meanings indicated above, in the presence of a base and in the presence of an inert organic diluent, at a temperature between 0° C. and 60° C.

15 Claims, No Drawings

PROCESS FOR THE PREPARATION OF OXIRANES

This is a continuation of application Ser. No. 603,524, filed Apr. 24, 1984, now abandoned.

The present invention relates to a new process for the preparation of known oxiranes which can be used as intermediates for the synthesis of compounds having plant-growth regulating and fungicidal activity.

It has already been disclosed that oxiranes can be prepared by converting dimethyl sulphoxide, using methyl iodide, into trimethyloxosulphonium iodide and reacting the latter with carbonyl compounds in the presence of a base (compare J. Amer. Chem. Soc. 87, 1353–1364 (1965)). Thus, for example, 2-(4-chlorophenoxymethyl)-2-tert.-butyloxirane can be synthesised by reacting trimethyloxosulphonium iodide, prepared from dimethyl sulphoxide and methyl iodide, with 1-(4-chlorophenoxy)-3,3-dimethyl-2-butanone in the presence of a strong base, such as, for example, sodium hydride or sodium amide, in the presence of an inert diluent, such as, for example, dimethyl sulphoxide (compare EP-OS (European Published Specification) No. 40,345). The yields in this process are good. However, it is a disadvantage that relatively costly methyl iodide is necessary for the preparation of the trimethyloxosulphonium iodide required as the starting material.

It has now been found that the known oxiranes of the formula

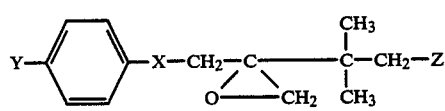

in which
Y represents chlorine or phenyl,
X represents oxygen or $CH_2$ and
Z represents hydrogen or halogen,
are obtained when dimethyl sulphoxide is treated with dimethyl sulphate, and the trimethyloxosulphonium methyl sulphate, which is thereby produced, of the formula $$(CH_3)_3SO^{\oplus}CH_3SO_4^{\ominus} \quad (II)$$

is reacted, without previous isolation, with a ketone of the formula

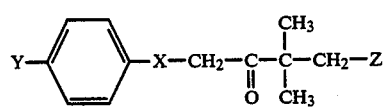

in which
X, Y and Z have the meanings indicated above,
in the presence of a base and in the presence of an inert organic diluent, at temperatures between 0° C. and 60° C.

The course of the process according to the invention has to be denoted extremely surprising. This is because it was known, from the state of the art, that, with alkylating reagents other than methyl iodide, dimethyl sulphoxide is as a rule not alkylated on the sulphur but, in an undesired manner, on the oxygen (compare "Sulfur Ylides in Organic Chemistry", Monography, Academic Press, 10 (1975)). Dimethyl sulphoxide can be alkylated on the sulphur in poor yields only when using a Lewis acid-alkyl halide complex. Thus, it had to be assumed that only methyl iodide is suitable as a methylating agent for the preparation of relatively large amounts of trimethyloxosulphonium salts. However, in contrast to expectation, the desired S-methylation succeeds without problems by the process according to the invention even when dimethyl sulphate is used.

The process according to the invention is distinguished by a number of advantages. Thus, it makes it possible to prepare oxiranes of the formula (I) in good yields. Moreover, the starting materials are relatively low-cost and also available on an industrial scale.

The oxiranes which can be prepared by the process according to the invention are defined by the formula (I). In this formula, X represents oxygen or the $CH_2$ group, and Y represents chlorine or phenyl. The radical Z preferably represents hydrogen, fluorine or chlorine.

When, in the process according to the invention, in addition to dimethyl sulphoxide and dimethyl sulphate, 1-(4-chlorophenoxy)-3,3-dimethyl-2-butanone is used as the starting material and sodium methylate is used as the base, then the course of the reaction can be illustrated by the diagram below:

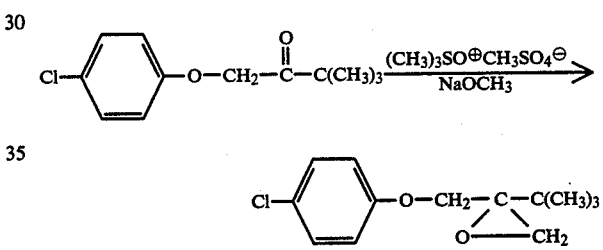

The ketones necessary as starting materials for the process according to the invention are defined by the formula (III). In this formula, Y represents chlorine or phenyl, and X represents oxygen or the $CH_2$ group. The radical Z preferably represents hydrogen, fluorine or chlorine.

The ketones of the formula (III) are known (compare German Patent Specification No. 2,201,063, DE-OS (German Published Specification) No. 2,705,678 and DE-OS (German Published Specification) No. 2,737,489).

In the process according to the invention, strong inorganic and organic bases can be used as the bases. Suitable and preferred are sodium hydride, sodium amide and alkali metal hydroxides, such as, for example, sodium hydroxide and potassium hydroxide, also alkali metal alcoholates, such as, for example, sodium methylate, sodium ethylate and potassium tert.-butylate.

All inert organic solvents can be used as the diluent for the process according to the invention, both for the preparation of the trimethyloxosulphonium methyl sulphate and for the subsequent reaction of the material with a ketone of the formula (III). Suitable and preferable are nitriles, such as acetonitrile, as well as polar solvents, such as dimethyl sulphoxide, also aliphatic or aromatic hydrocarbons, such as hexane, benzene, toluene or xylene. Separate addition of a diluent is unnecessary in the preparation of the trimethyloxosulphonium methyl sulphate when dimethyl sulphoxide is used in sufficient excess.

The reaction temperatures for carrying out the process according to the invention can be varied within a certain range. For the preparation of the trimethyloxosulphonium methyl sulphate, the temperatures are generally between 20° C. and 120° C., preferably between 60° C. and 110° C. For the subsequent reaction of the trimethyloxosulphonium methyl sulphate, the temperatures are generally between 0° C. and 60° C., preferably between 5° C. and 40° C.

The process according to the invention is generally carried out under normal pressure. However, it is also possible to carry it out under elevated or reduced pressure.

On carrying out the process according to the invention, in the first step 1 to 5 mole, preferably 1.5 to 4 mole, of dimethyl sulphoxide is generally employed for 1 mole of dimethyl sulphate. In the second step, the amounts of the components in the reaction are generally selected such that 1.0 to 1.5 mole, preferably 1.1 to 1.3 mole, of trimethyloxosulphonium methyl sulphate and 1.5 to 2.5 mole, preferably 1.6 to 2.0 mole, of base are present for 1 mole of ketone of the formula (III).

The specific procedure for carrying out the process according to the invention is such that dimethyl sulphate and dimethyl sulphoxide are mixed, optionally in the presence of an additional diluent, the mixture is heated, then cooled and a solution of a ketone of the formula (III) in an organic solvent is added and then the base is added. Working up is carried out by customary methods. In general, the procedure is such that water is added to the reaction mixture, the resulting mixture is, if necessary, stirred with active charcoal and filtered through kieselguhr, then the organic phase is separated off, washed and evaporated after previous drying if necessary. The product resulting thereby can be distilled under reduced pressure for further purification.

The oxiranes of the formula (I) which can be prepared by the process according to the invention are valuable starting materials for the synthesis of 1-hydroxyethylazole derivatives which have outstanding plant-growth regulating and fungicidal properties (compare EP-OS (European Published Specification) No. 40,345).

Thus, for example, 2-(4-chlorophenoxymethyl)-3,3-dimethyl-1-(1,2,4-triazol-1-yl)-2-butanol of the formula

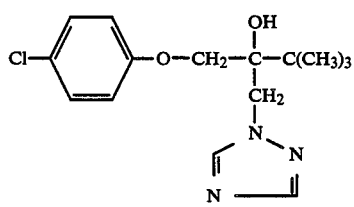

can be prepared by reacting 2-(4-chlorophenoxymethyl)-2-tert.-butyloxirane with 1,2,4-triazole in the presence of ethanol. This synthesis can be illustrated by the formulae below:

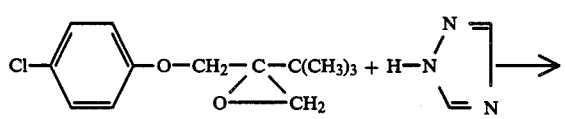

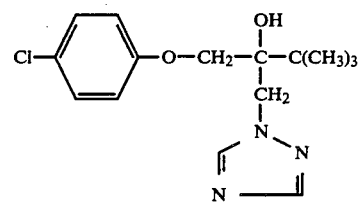

The process according to the invention is illustrated by the examples which follow.

EXAMPLE 1

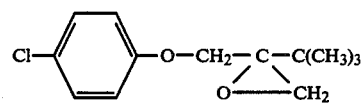

A mixture of 71 ml (78 g; 1 mole) of dimethyl sulphoxide and 28.7 ml (37.8 g; 0.3 mole) of dimethyl sulphate was heated to 100° C. and kept at this temperature for 30 minutes. After cooling to room temperature, a solution of 57 g (0.25 mole) of 1-(4-chlorophenoxy)-3,3-dimethyl-2-butanone in 100 ml of toluene was added dropwise with stirring. This reaction mixture was then cooled to 10° C., and 25 g (0.46 mole) of sodium methylate were added in portions, with stirring. The mixture was subsequently stirred a further 12 hours at room temperature and then 100 ml of water were added. The resulting mixture was thoroughly stirred with 0.5 g of active charcoal and filtered through kieselguhr. The organic phase was then separated off, washed twice with 100 ml of water each time and evaporated under reduced pressure. A residue of 55.3 g remained, which, according to the gas chromatogram, consisted of 71% of 2-(4-chlorophenoxymethyl)-2-tert.-butyloxirane. A yield of 65.2% of theory was calculated from this. Example for the use of an oxirane which can be prepared according to the invention for the synthesis of a 1-hydroxyethylazole derivative having plant-growth regulating and fungicidal activity.

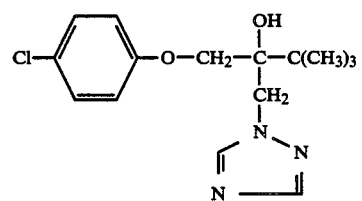

A mixture of 72.15 g (0.3 mole) of 2-(4-chlorophenoxymethyl)-2-tert.butyloxirane and 24.15 g (0.35 mole) of 1,2,4-triazole in 120 ml of ethanol was heated under reflux for 48 hours. It was then evaporated and the residue remaining was taken up in 200 ml of ethyl acetate. The resulting mixture was first preheated and then cooled in an ice bath. The solid precipitating thereby was filtered off with suction and washed with ethyl acetate. The filtrate was evaporated, the residue remaining was dissolved in a mixture of ether and hexane, and gaseous hydrogen chloride was passed into the resulting solution. A precipitate formed during this, and was filtered off with suction and washed with ether. The free base from which the salt thus prepared was derived was liberated by addition of ethyl acetate and 1N aqueous sodium hydroxide solution. In this manner, 60.2 g (65% of theory) of 2-(4-chlorophenoxymethyl)-3,3-dimethyl-1-(1,2,4-triazol-1-yl))-2-butanol, of melting point 84°-87° C., were obtained.

What is claimed is:

1. A process for the preparation of an oxirane of the formula

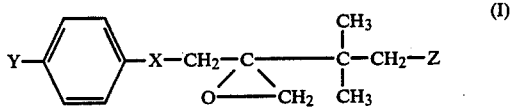

ps in which

Y represents chlorine,

X represents oxygen and

Z represents hydrogen which comprises contacting dimethyl sulphoxide with dimethyl sulphate at a temperature of at least 100° C., whereby to form trimethyloxosulphonium methyl sulphate of the formula

and thereafter, without isolating said trimethyloxosulphonium methyl sulphate, contacting the trimethyloxosulphonium methyl sulphate with a ketone of the formula

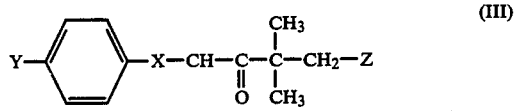

in which

X, Y and Z have the meanings indicated above, in the presence of a base and in the presence of an inert organic diluent, at a temperature between 0° C. and 60° C.

2. A process according to claim 1 wherein the reaction of the trimethyloxosulphonium methyl sulphate with the ketones is carried out at a temperature between 5° C. and 40° C.

3. A process according to claim 1 wherein the organic diluent is selected from the group consisting of acetonitrile, dimethyl sulphoxide and toluene.

4. A process according to claim 1 wherein said base is selected from the group consisting of sodium hydride, sodium amide, sodium hydroxide, potassium hydroxide and alkali metal alcoholates.

5. A process according to claim 1 wherein 1 to 5 moles of dimethyl sulphoxide are employed per mole of dimethyl sulphate.

6. A process according to claim 4, wherein said alkali metal alcoholates are selected from the group consisting of sodium methylate, sodium ethylate and potassium tert.-butylate.

7. A process according to claim 1, wherein the contacting of the dimethyl sulphoxide and the dimethyl sulphate is conducted at a temperature up to 120° C.

8. A process according to claim 1, wherein the contacting of the dimethyl sulphoxide and the dimethyl sulphate is conducted at a temperature up to 110° C.

9. A process according to claim 1, wherein the process is conducted at normal pressure.

10. A process according to claim 1, wherein the process is conducted at reduced pressure.

11. A process according to claim 1, wherein the process is conducted at elevated pressure.

12. A process according to claim 1, wherein 1.5 to 4 moles of said dimethyl sulphoxide are employed per mole of said dimethyl sulphate.

13. A process according to claim 1, wherein 1.0 to 1.5 moles of said trimethyloxosulphonium methyl sulphate, and 1.5 to 2.5 moles of said base are employed per mole of said ketone.

14. A process according to claim 1, wherein 1.1 to 1.3 moles of said trimethyloxosulphonium methyl sulphate, and 1.6 to 2.0 moles of said base are employed per mole of said ketone.

15. A process according to claim 1, wherein the dimethyl sulphate and the dimethyl sulphoxide are mixed, the resultant mixture is heated and then cooled, a solution of the ketone in the organic diluent is added and then the base is added.

* * * * *